United States Patent
Ganesh et al.

(10) Patent No.: US 6,971,850 B2
(45) Date of Patent: Dec. 6, 2005

(54) MULTIPLE ALLOY ROTOR AND METHOD THEREFOR

(75) Inventors: Swami Ganesh, Clifton Park, NY (US); Robin Carl Schwant, Pattersonville, NY (US); Ling Yang, Niskayuna, NY (US); John Zhiqiang Wang, Greenville, SC (US)

(73) Assignee: General Electric Company, Schenectady, NY (US)

( * ) Notice: Subject to any disclaimer, the term of this patent is extended or adjusted under 35 U.S.C. 154(b) by 94 days.

(21) Appl. No.: 10/707,306

(22) Filed: Dec. 4, 2003

(65) Prior Publication Data

US 2005/0095137 A1 May 5, 2005

Related U.S. Application Data

(63) Continuation-in-part of application No. 10/463,441, filed on Jun. 18, 2003, now Pat. No. 6,807,860.

(51) Int. Cl.[7] .................................................. F01D 5/06
(52) U.S. Cl. .................................................. 415/216.1
(58) Field of Search ............................. 415/200, 216.1; 148/325, 335, 428; 420/34, 27, 36, 69, 70, 47, 446

(56) References Cited

U.S. PATENT DOCUMENTS

| 5,487,082 A | | 1/1996 | Takenouchi et al. ........... 373/42 |
| 5,524,019 A | * | 6/1996 | Takenouchi et al. ........... 373/54 |
| 6,092,989 A | * | 7/2000 | Siga et al. .................... 415/200 |
| 6,350,325 B1 | | 2/2002 | Ewald et al. ................. 148/325 |
| 6,499,946 B1 | | 12/2002 | Yamada et al. ........... 415/199.4 |

* cited by examiner

*Primary Examiner*—Ninh H. Nguyen
(74) *Attorney, Agent, or Firm*—David L. Narciso; Gary M. Hartman; Domenica N. S. Hartman

(57) ABSTRACT

A process for producing a rotor, the rotor formed thereby, as well as turbines in which such a rotor is installed. The rotor is formed by casting an ingot to have first and second regions formed of different alloys that intermix during casting to define a transition zone therebetween. The ingot is forged to yield a rotor forging that contains axially-aligned first and second alloy regions and a transition zone therebetween. The effects of the transition zone can be mitigated by modeling the transition zone and then off-center machining the forging so that the axis of rotation of the machined monolithic rotor is more centrally located with respect to the transition zone.

9 Claims, 5 Drawing Sheets

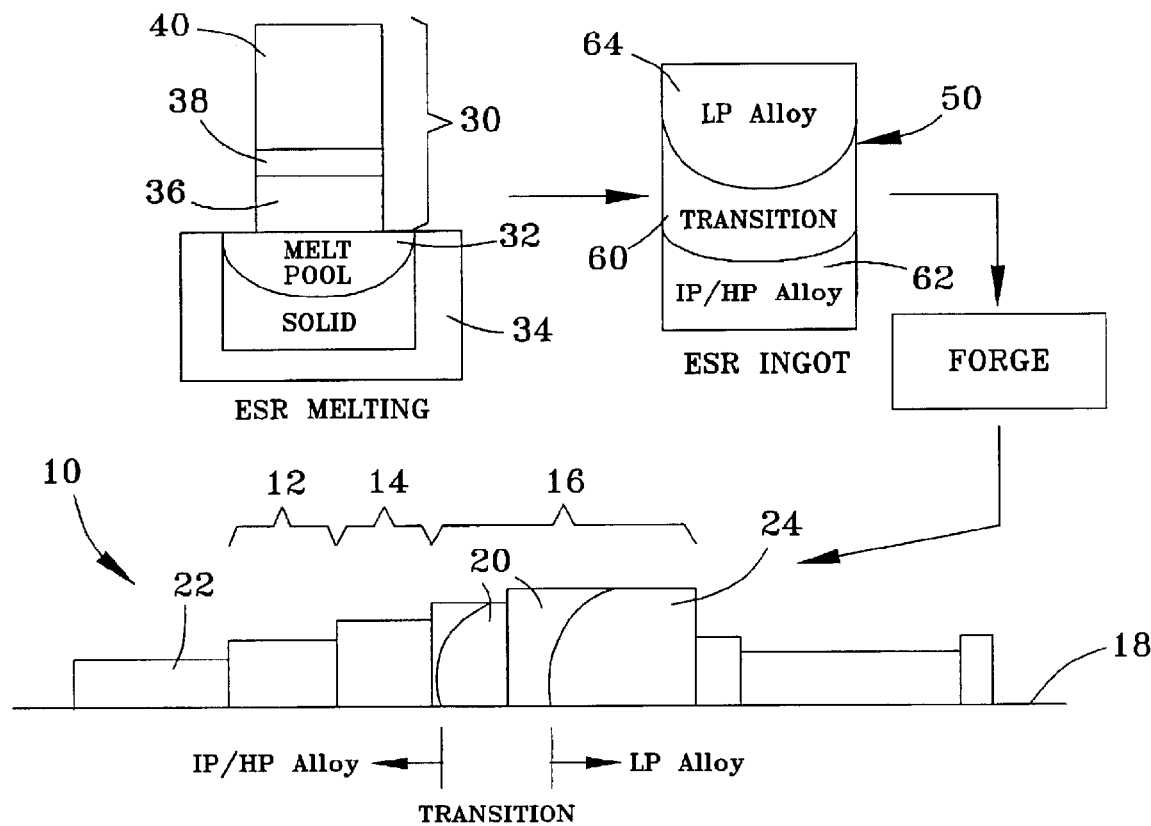
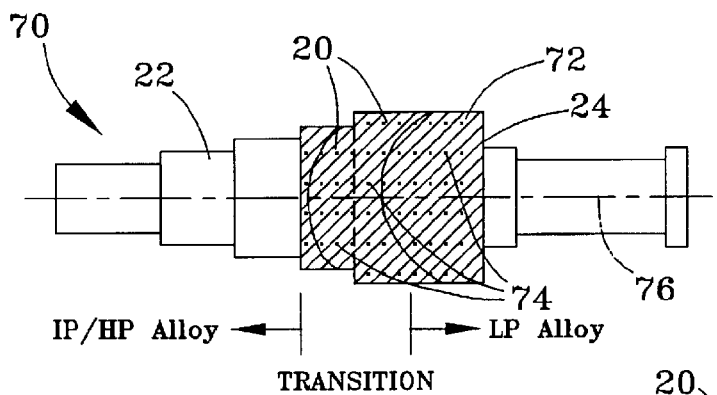
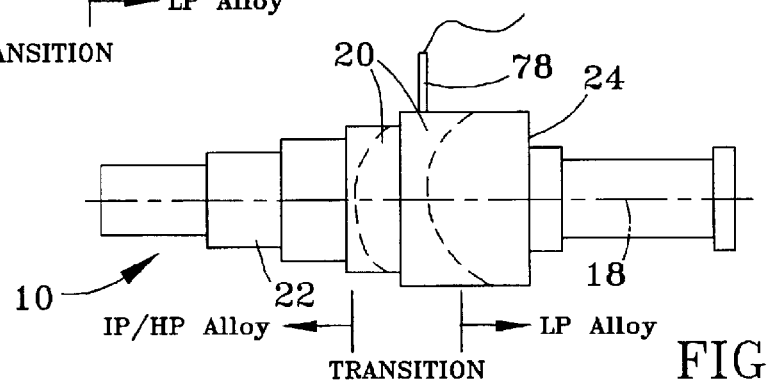

MULTIPLE ALLOY ROTOR AND METHOD THEREFOR

CROSS REFERENCE TO RELATED APPLICATIONS

This is a continuation-in-part patent application of U.S. patent application Ser. No. 10/463,441, filed Jun. 18, 2003 now U.S. Pat. No. 6,807,860.

BACKGROUND OF INVENTION

1. Field of the Invention

The present invention generally relates to turbine rotors, such as those used in steam turbines, gas turbine engines, and jet engines. More particularly, this invention relates to a rotor and method of producing a monolithic rotor containing two or more alloys within separate regions of the rotor resulting in a transition zone between different alloy regions, and to a method of determining the shape of the transition zone to enable the final machined geometry of the rotor to reduce any thermal instability attributable to the presence of the transition zone.

2. Description of the Related Art

Rotors used in steam turbines, gas turbines and jet engines typically experience a range of operating conditions along their lengths. The different operating conditions complicate the selection of a suitable rotor material and the manufacturing of the rotor because a material optimized to satisfy one operating condition may not be optimal for meeting another operating condition. For instance, the inlet and exhaust areas of a steam turbine rotor have different material property requirements. The high temperature inlet region typically requires a material with high creep rupture strength but only moderate toughness. The exhaust area, on the other hand, does not demand the same level of high temperature creep strength, but suitable materials typically must have very high toughness because of the high loads imposed by long turbine blades used in the exhaust area.

Because a monolithic rotor (i.e., a rotor that is not an assembly) of a single chemistry cannot meet the property requirements of each of the LP, IP and HP stages for the reasons discussed above, rotors constructed by assembling segments of different chemistries are widely used. For example, large steam turbines typically have a bolted construction made up of separate rotors contained in separate shells or hoods for use in different sections of the turbine. More recently, the steam turbine industry has favored CrMoV low alloy steels for use in the HP stage and NiCrMoV for use in the LP stage, though NiMoV low alloy steels have also been widely used as materials for the various stages. Smaller steam turbines may make use of a mid-span coupling to bolt high and low temperature components together within one shell. Finally, rotors for gas turbines and jet engines are often constructed by bolting a series of disks and shafts together. While rotors having a bolted construction are widely used, they suffer from several disadvantages including increased numbers of parts, increased assembly requirements, increased length of the rotor assembly, and more balance complexity.

Another method of combining different materials in a single rotor is to weld together rotor segments formed of dissimilar materials, forming what may be termed a multiple alloy rotor (MAR). However, a welded rotor construction also has disadvantages, such as high investment costs for the welding equipment, additional production costs for weld preparation and welding, long production times to produce, inspect and upgrade the weld, and increased cost and production time caused by the need for post weld heat treatment. The strength of rotors having a welded construction can also be limited due to a need to maintain a low carbon content in the weld, and the propensity for high numbers of small non-metallic inclusions that reduce load carrying capability.

The capability of producing a monolithic MAR would address the above-noted shortcomings of assembled MAR's. Furthermore, monolithic MAR's would be particularly well suited for meeting the demand for higher efficiency steam turbines whose requirements include low pressure (LP), intermediate pressure (IP) and high pressure (HP) stages (or combinations thereof) with additional stages in areas normally occupied by couplings. Consumable electrode remelting techniques such as electro-slag remelting (ESR) and vacuum arc remelting (VAR) methods offer flexibility for producing components that contain alloy combinations, and therefore has been considered for producing monolithic MAR's. As an example, U.S. Pat. No. 6,350,325 to Ewald et al. discloses an ESR method of producing a dual alloy rotor from 12Cr-type alloys that have different levels of alloying constituents, but are sufficiently close in composition so as to have substantially identical austenitizing temperatures. Ewald et al. also disclose that, because the alloys have similar compositions, problems can be avoided that are associated with mixing of alloys having significantly different material properties, which results in the formation of a transition zone (TZ) between regions of the rotor formed by the different alloys.

One such problem is thermal stability arising from the massive size of a rotating rotor supported by bearings at each end of the rotor. When supported in this manner, a rotor behaves as a simply supported beam structure and will deflect in reaction to the centrifugal load always present at operational conditions, with the largest deflection being near the center of the rotor. Because of the inherent asymmetry of the transition zone within a MAR rotor, deflection significantly increases when the rotor is at its elevated operating temperatures. As the rotor rotates about its bent centerline, the rotor material is subjected to high cycle fatigue as a result of being in tension and then in compression with each rotation. Consequently, reducing deflection by minimizing material asymmetry is necessary to maximize the life of a MAR rotor and the turbine in which it is installed. One solution is to limit the rotor to alloys with similar compositions. However, this restriction limits the ability to optimize the compositions of the LP, IP and HP rotor sections for their operating environments and cost. For example, such a limitation has dissuaded the manufacture of a monolithic MAR whose HP stage is formed of CrMoV and its LP stage is formed of NiCrMoV. Therefore, it would be desirable if an improved process were available for producing turbine rotors of different alloy compositions.

SUMMARY OF INVENTION

The present invention provides a process for producing a rotor, the rotor formed thereby, as well as turbines in which such a rotor is installed. The rotor is formed by machining a single rotor forging to have at least two axially-aligned rotor regions and a transition zone therebetween. According to a particular aspect of the invention, the rotor is a monolithic multiple alloy rotor (MAR), wherein the rotor regions are formed of different alloys and the transition zone has a composition that differs from and varies between the rotor regions.

The process of this invention involves casting a multiple-alloy ingot having at least first and second ingot regions axially aligned within the ingot, with the first and second ingot regions being formed of different alloys so that intermixing occurs during casting to define a transition zone therebetween having a composition that differs from and varies between the first and second ingot regions. The ingot is then forged to produce a rotor forging containing first and second forging regions and a transition zone therebetween corresponding to the first and second ingot regions and the transition zone of the ingot, i.e., the first and second forging regions are formed of the different alloys and the transition zone of the rotor forging has a composition that differs from and varies between the first and second forging regions. The first and second forging regions and the transition region therebetween are axially aligned along a geometric centerline of the rotor forging. Following heat treatment, the rotor forging is machined to produce a machined rotor containing first and second rotor regions and a transition zone therebetween corresponding to the first and second forging regions and the transition zone of the rotor forging, i.e., the first and second rotor regions are also formed of the different alloys and the composition of the transition zone within the machined rotor differs from and varies between the first and second rotor regions.

According to one aspect of the invention, the transition zone within the rotor forging is asymmetrical about the geometric centerline of the rotor forging. This asymmetry of the transition zone may be attributable to asymmetry of the transition zone within the ingot and/or as a result of the forging operation, the latter of which always degrades the symmetry of the transition zone to some degree. Because the material properties of the rotor vary with the composition of the transition zone, asymmetry of the transition zone causes asymmetrical variations in the mechanical and physical properties of the rotor, which if not mitigated promotes bending of the rotor and thermal instability during operation. According to the invention, the asymmetry of the transition zone is mitigated by producing a three-dimensional approximation of the shape of the transition zone, and then using the three-dimensional approximation to predict deflection of the geometric centerline of the rotor forging if the forging were to be heated to an elevated temperature. The three-dimensional approximation of the shape of the transition zone can be produced by combining measurements of the chemistry on the surface of the rotor with either knowledge of the shape of the solidified transition zone melt pool after forging or by ultrasonic inspection to identify the three-dimensional shape of the transition zone. With this knowledge, the rotor forging can be machined so that its axis of rotation is more centrally located with respect to the transition zone of the rotor, and therefore more centrally located with respect to the material properties of the rotor. As an optional additional step following rough machining of the rotor forging, a standard heat indication test can be performed on the rotor to measure its tendency to bend when heated and, if the tendency is larger than desired, the results of the heat indication test can be used to optimize the final machining of the rotor to reduce the bending tendency.

In view of the above, it can be seen that a significant advantage of this invention is that a multiple alloy rotor can be produced by casting and forging without the limitations previously placed on the alloys used to form such rotors. In particular, the present invention permits the use of dissimilar alloys such as NiCrMoV and CrMoV alloys, which form transition zones that, using prior art processing approaches, would result in a rotor that exhibits unacceptable thermal instability. The invention is able to over-come this restriction with a process that reduces the asymmetrical property variations attributable to the transition zone, thereby permitting different sections of the rotor to be formed of alloys that have the potential for optimizing the different rotor sections (e.g., HP, IP, and LP) for their operating environments.

Other objects and advantages of this invention will be better appreciated from the following detailed description.

BRIEF DESCRIPTION OF DRAWINGS

FIG. 1 schematically represents processing steps performed to produce a multiple alloy rotor forging having a transition zone in accordance with a preferred embodiment of this invention.

FIG. 2 schematically represents a partial cross-sectional view of a rotor forging formed by the process of FIG. 1, wherein chemical analysis is performed at points within and adjacent the transition zone in accordance with an embodiment of the invention.

FIG. 3 shows a rotor forging formed by the process of FIG. 1, wherein metallurgical characteristics within and adjacent the transition zone are determined by ultrasonic inspection in accordance with another embodiment of the invention.

DETAILED DESCRIPTION

Figure 4:
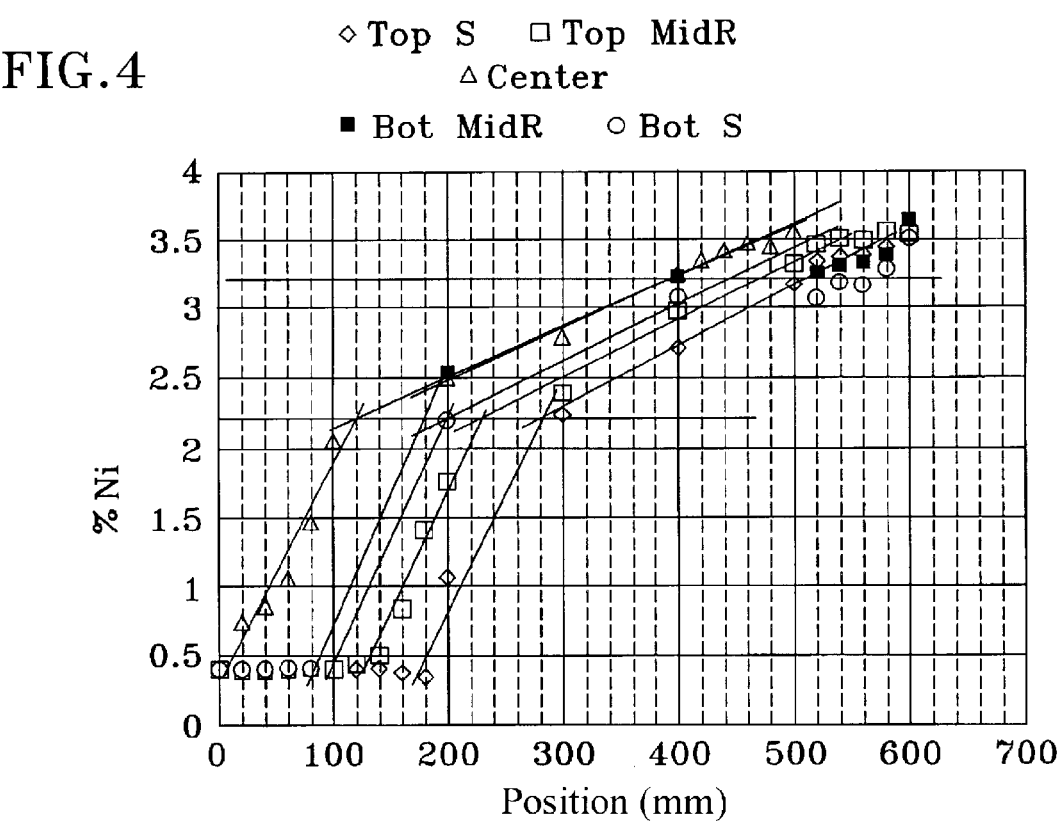
FIG. 4 is a chart showing data collected from chemical analysis of a rotor forging in accordance with the embodiment of FIG. 2.

The present invention generally pertains to the production of a multiple alloy rotor (MAR) using a casting technique, preferably a consumable electrode remelting technique such as electro-slag remelting (ESR) or vacuum arc remelting (VAR), and various combinations of alloy chemistries to achieve properties suitable for different regions of the rotor, such as the high, intermediate and low pressure turbine stages of an advanced power generation steam turbine, gas turbine, or aircraft engine. In so doing, a transition zone is present within the rotor between regions that have substantially uniform compositions that differ from region to region.

FIG. 1 represents such a process, by which a monolithic (one-piece) rotor forging 10 is produced by ESR in accordance with the invention. The forging 10 (of which only half is depicted in FIG. 1) is represented as having been rough machined to define high pressure (HP), intermediate pressure (IP), and low pressure (LP) sections 12, 14 and 16, respectively, along a geometric centerline 18 of the forging 10. The forging 10 is also represented as having a transition zone 20 between two regions 22 and 24 of the forging 10 formed of an IP/HP Alloy and an LP Alloy, respectively. FIG. 1 shows the LP alloy region 24 and the transition zone 20 generally limited to the LP section 16 of the forging 10, while the IP/HP alloy region 22 is generally limited to the HP and IP sections 12 and 14 of the forging 10. Various other configurations are possible, e.g., the transition zone 20 could extend into the IP section 14 of the forging 10. The alloys are preferably selection to have mechanical and physical properties that are optimized for their respective locations within a rotor that will be subsequently machined from the forging 10. As such, the IP/HP and LP alloy compositions are different but substantially uniform within their respective regions 22 and 24. In contrast, the composition within the transition zone 20 varies between each of its boundaries with the regions 22 and 24 in view of the compositional differences between the LP and IP/HP alloys and the process by which the forging 10 is cast.

As with conventional ESR techniques, FIG. 1 shows an electrode 30 suspended over a melt pool 32 contained in a chilled crucible 34. In the ESR process, resistance heating between the electrode 30 and molten slag (not shown) on the surface of the pool 32 causes melting of the electrode 30. During melting, molten droplets of the electrode 30 drop through the slag, where they solidify to produce a directionally solidified ingot 50 having discrete regions 60, 62 and 64 along its axial length. The electrode 30 is depicted as comprising least three distinct regions 36, 38 and 40. The lower and upper regions 36 and 40 of the electrode 30 are formed of alloys corresponding to the IP/HP and LP alloys desired for the regions 22 and 24 of the forging 10. In accordance with an optional aspect of the invention, the intermediate region 38 of the electrode 30 may have a composition that differs from the other two electrode regions 36 and 40 for the purpose of tailoring the composition of the transition zone 20 within the forging 10. The regions 36, 38 and 40 of the electrode 30 can be produced using air or vacuum melting processes, followed by the use of a welding process or an ESR or VAR process to join the regions 36, 38 and 40 end-to-end. Alternatively, a separate piece of each alloy could be melted individually and in sequence to form the ingot 30.

As the process of the invention is represented in FIG. 1, the lower region 62 of the ingot is represented as being formed by the IP/HP alloy (lower region 36) of the electrode 30, and the upper region 64 is indicated as being formed by the LP alloy (region 40) of the electrode 30, though the order of the IP/HP and LP alloys could be reversed from that shown. The lower and upper regions 36 and 40 of the electrode 30 have lengths appropriate to create the corresponding regions 62 and 64 within the ingot 50. The middle region 60 of the ingot 50 is a transition zone between the regions 62 and 64. Regardless of whether the electrode 30 includes the intermediate region 38, the transition zone 60 inherently forms as a result of intermixing of the IP/HP and LP alloys during the ESR process. If the electrode 30 is formed to include the intermediate region 38, the intermediate region 38 can be formulated to have a special intermediate chemistry to control the chemistry gradient and/or the width of the transition zone 60 within the ingot 50. However, the shape and size of the transition zone 60 cannot be precisely controlled in view of variables in the ESR process. Therefore, the transition zone 60 may have a shape whose axial boundaries, though corresponding to the shape of the melt pool 32, can be asymmetrical to some degree about the axis of the ingot 50. The regions 60, 62 and 64 of the ingot 50 form the transition zone 20 and the regions 22 and 24, respectively, of the rotor forging 10 forged from the ingot 50. Of particular significance to the present invention, any forging operation performed on the multiple-alloy ingot 50 of this invention will inherently degrade the symmetry of the transition zone 60 within the ingot 50, such that the shape of the transition zone 20 within the rotor forging 10 can be significantly asymmetrical relative to the centerline 18 of the forging 10.

Various characteristics are required for the different sections 12, 14 and 16 of the forging 10 in order to meet the properties required of a rotor machined from the forging 10, such as tensile strength, fracture toughness, rupture strength, thermal stability, and high process capability (repeatability and reproducibility), as well as cost targets. In order to achieve the mechanical properties desired for the rotor, the chemistries of the multiple alloys of the forging 10 are likely to be sufficiently different to require different heat treatment temperatures and durations, such that a differential heat treatment must be performed on the forging 10 prior to machining. For this purpose, a furnace with multiple temperature zones is used to provide an appropriate heat treatment temperature for each region 20, 22 and 24 of the rotor forging 10. The heat treatment may include a differential temperature for both the solution or austenitizing treatment and the aging or tempering treatment of the particular alloys. For steels, a higher temperature austenitizing treatment is preferably used if higher creep rupture strength is desired (e.g., for the high pressure rotor section 12), while relatively lower temperatures are used if higher toughness is needed (e.g., for the low pressure rotor section 16). Differential cooling from the solution or austenitizing temperature is also preferably used. Rapid cooling can be used to achieve full section hardening, to avoid harmful precipitation reactions, and/or to enhance toughness (e.g., for the low pressure rotor section 16). Slow cooling can be used to achieve beneficial precipitation reactions, to reduce thermal stresses, and/or to enhance creep rupture strength (e.g., for the high pressure rotor section 12). Particular temperatures, durations, and heating and cooling rates suitable for the forging 10 will depend on the materials used, and such heat treatment parameters will generally be within the capability of one skilled in the art.

Notable commercial alloys that are suitable for use as the LP alloy include the conventional NiCrMoV-type low alloy steels and chromium-containing martensitic stainless steels such as the 12Cr—3Ni—Mo—V type alloy (M152). Alloys that are suitable for use as the IP/HP alloy of the IP and HP sections 12 and 14 include a variety of alloys having increasing high temperature capability, such as the conventional CrMoV low alloy steels, 9–14 Cr-type alloys with varying levels of Mo, V, W, Nb, B and N, Fe—Ni alloys (such as A286), and nickel-base alloys (such as Alloy 706 or 718). Particularly preferred alloys for the LP section 16 include the following:

TABLE 1

| ALLOY TYPE | COMPOSITION (approximate by weight) |
|---|---|
| NiCrMoV low alloy steel | 2–4 Ni, 1–2 Cr, 0.2–0.5 Mo, 0.05–0.2 V, 0.18–0.35 C, balance Fe and incidental impurities. |
| Martensitic stainless steel | 2–3.5 Ni, 11–14 Cr, 0.2–1.2 Mn, 1–2.5 Mo, 0.2–0.5 V, 0.05–0.2 C, balance Fe and incidental impurities. |

Particularly preferred alloys for the HP and IP sections 12 and 14 include the following:

TABLE 2

| ALLOY TYPE | COMPOSITION (approximate by wt. %) |
|---|---|
| CrMoV low alloy steel | 0.25–0.75 Ni, 0.8–2.5 Cr, 0.5–1 Mn, 1–2.5 Mo, 0.2–0.35 V, 0.15–0.35 C, balance Fe and incidental impurities. |
| Martensitic stainless steel | 0–1.3 NI, 9–14 Cr, 0.1–1 Mn, 0.2–2 Mo, 0.1–0.7 V, 0–3 W, 0–6 Co, 0.03–0.20 C, balance Fe and incidental impurities. |
| Fe—Ni alloy | 24–27 Ni, 13–16 Cr, 1.8–2.5 Ti, 1–1.5 Mo, 0.1–0.5 V, less than 2 Mn, less than 1 Si, less than 0.5 Al, less than 0.08 C, balance Fe and incidental impurities. |
| Nickel-Base Alloy | 16–20 Fe, 17–21 Cr, 2.5–3.5 Mo, 4.5–5.5 Nb, 0.6–1.2 Ti, 0.2–0.8 Al, 0–1 Co, less than 0.35 Mn, less than 0.35 SI, less than 0.08 C, balance Ni and incidental impurities. |

On the basis of combinations of the above alloys, chemistries that are believed to be well suited for the intermediate region 38 of the electrode 30 include the following:

TABLE 3

| ALLOY COMBINATION (LP Alloy - HP/IP Alloy) | COMPOSITION (approximate by wt. %) |
|---|---|
| NiCrMoV—CrMoV | 0.25–8 Ni, 0.8–6 Cr, 0.2–1.0 Mn, 0.2–1.5 Mo, 0.05–0.35 V, 0.1–0.4 C, balance Fe and incidental impurities. |
| NiCrMoV - Martensitic | 4–8 Ni, 0–1 Mn, 14–30 Cr, 1.5–5 Mo, 3–7 W, 4–12 Co, 0.2–0.35 C, balance Fe and incidental impurities. |
| NiCrMoV—FeNi alloy | 16–32 Cr, 1–4 Mn, 1.5–4 Mo, 0.1–1.0 V, 0–0.5 Al, 0.5–5 Ti, 0–2 Si, 0–0.08 C, balance Ni and incidental impurities. |
| NiCrMoV—Ni alloy | 0–20 Fe, 15–40 Cr, 0–0.35 Mn, 2–10 Mo, 3–12 Nb, 0–2 Al, 0–3 Ti, 0–1 Co, 0.01–0.08 C, balance (30–60) Ni and incidental impurities. |
| Martensitic - Martensitic | 0.5–8 Ni, 9–18 Cr, 0–4 Mn, 0.8–4 Mo, 0.1–0.5 V, 0–0.5 Al, 0.02–0.05 N, 0.15–0.35 C, balance Fe and incidental impurities. |
| Martensitic - FeNi alloy | 0–60 Ni, 9–24 Cr, 0.5–2.0 Mn, 0.5–3.0 Mo, 0–0.5 V, 0.01–0.35 C, balance Fe and incidental impurities. |
| Martensitic - Alloy 718 | 8–12 Cr, 0.5–1.2 Mn, 0–2 Mo, 0.2–0.5 V, 0–1 Co, 0.01–0.20 C, balance Fe and incidental impurities. |
| Martensitic - Alloy 718 | 9–50 Cr, 0–2.0 Mn, 0–8 Mo, 0–12 Nb, 0–2 Al, 0–3 Ti, 0–1 Co, 0.01–0.08 C, balance Fe and incidental impurities. |

The ability to produce a monolithic multiple alloy rotor as described above provides various advantages. For example, fewer parts are required to produce a rotor as compared to prior art rotors produced by bolting or welding rotor sections together. Additional machining that would otherwise be required to prepare the parts for assembly is not required, and the steps of assembling and welding the parts together is eliminated. Each of these advantages reduces the cost and time required to produce a rotor. By eliminating the assembly requirement, the overall length of a rotor does not need to be increased in order to accommodate a mid-span coupling, thereby minimizing related expenses such as turbine shell and site preparation costs. The ability to avoid a welding operation eliminates the requirement for a post-weld heat treatment, which is otherwise required in addition to the heat treatment performed after forging. By eliminating welding, the strength level of the rotor can be higher than that of a rotor with a welded-type construction because there are no limitations on chemical composition other than the limitations normally imposed on ingot making.

Facility costs are also reduced by eliminating the requirement for specialized welding equipment to weld a rotor, which is particularly significant if a massive steam rotor is being produced. Notably, existing consumable electrode remelting (ESR and VAR) furnaces are capable of producing rotors. Consumable electrode remelting is also advantageous in that it provides a rotor that is essentially free from small nonmetallic inclusions commonly found in welded construction and which if present can reduce load-carrying capability. Grinding and repair welding to upgrade defective welded rotor joints will not be required thus saving cost and production time. Little or no alloy development is needed because alloys that are currently joined by assembly, welding, etc., can be employed by this invention.

As discussed above, the different chemistries of the alloys within the sections 12, 14 and 16 of the rotor forging 10 result in the formation of the transition zone 20, whose properties and shape affect the dynamics of the rotor machined from the forging 10. In particular, the transition zone 20 affects the thermal stability of the rotor at high temperatures, characterized by rotor centerline deflection that is detrimental to rotor balance, turbine clearance, and high cycle fatigue life. While consumable electrode remelting techniques are able to minimize the amount of molten metal that exists at any time in the ingot crucible 34, and thereby limit the axial extent over which alloy mixing will occur, a transition zone of some size and shape will be present within the ingot 50 and therefore within the forging 10, particularly in view of the significant differences in the preferred alloys identified in Tables 1 and 2. Optimum chemistries for the electrode's intermediate region 38 (Table 3) can have the effect of minimizing the extent of the transition zones 20 and 60, thus reducing thermal stability attributable to the transition zone 20 in the forging 10. The chemistry of the electrode's intermediate region 38 can also be optimized so as to limit the extent of the transition zone 20 to assist in locating the boundaries of the chemistries of the forging regions 22 and 24. Nonetheless, forging of the multiple-alloy ingot 50 to produce the rotor forging 10 will result in the transition zone 20 having an asymmetrical shape and therefore asymmetrical material properties that negatively affect the dynamics of a rotor machined from the forging 10.

Accordingly, a preferred aspect of the invention is to mitigate the detrimental effect of the transition zone 20 by minimizing the material asymmetry within the rotor near and within the transition zone 20, thus reducing centerline deflection of the rotor when it is heated to its operating temperatures. For this purpose, the present invention preferably includes the step of altering the geometry of the machined rotor relative to that of the rotor forging 10 by off-center machining, so that the centerline of the final machined geometry of the rotor is relocated from that of the forging 10 to minimize the adverse effects of the inhomogeneity of the rotor around the transition region 20. To determine the extent of off-center machining required, the three-dimensional shape of the transition zone 20 is determined using a suitable approximation technique. For example, boundary points of the transition zone 20 within the rough-machined forging 10 can be ascertained to define a plurality of axially-spaced, two-dimensional cross-sectional shapes of the transition zone 20. These two-dimensional cross-sectional shapes can then be used to generate the three-dimensional shape of the transition zone 20, and finite element modeling (FEM) or another suitable analytical technique can be performed on the three-dimensional shape to predict the deflection of the geometric centerline (axis of rotation) of a rotor machined from the forging 10. With this information, the centerline of the machined rotor can be shifted by off-center machining to reduce deflection.

Various techniques could be used to develop both two and three-dimensional shapes of the transition zone 20 within the rotor forging 10. According to one embodiment of the invention, the three dimensional shape of the transition zone 20 is approximated by measuring the variation of chemistry at the outer surface of the rough-machined rotor forging 10, combined with information about the likely shape of the transition zone 20 obtained by sectioning another rotor that was cast and forged under similar or identical conditions. With this approach, an axial-spaced series of two-dimensional shapes is generated by longitudinally sectioning the similarly-processed rotor forging specimen along its geometric centerline, and then detecting the level of one or more alloying constituents present in the forging specimen to identify the boundaries separating the transition zone from the adjacent regions of the specimen. Such a technique is represented in FIG. 2, in which a rough-machined forging specimen 70 is depicted as containing a transition zone between two axially-aligned regions of dissimilar alloys (identified with the same reference numbers as used in FIG. 1 for convenience). FIG. 2 represents a portion of the forging specimen 70 as having been cross-sectioned to expose a diametrical sectioned surface 72 of the specimen 70. The chemistries of the transition zone 20 and adjacent portions of the regions 22 and 24 are then determined at any number of locations 74 on the sectioned surface 72. The locations 74 are aligned along radials of the forging specimen 70, with the locations 74 being sufficiently close within each radial and sufficiently close along the axis 76 of the specimen 70 to be able to detect changes in one or more of the alloying constituents, e.g., nickel, within each region 20, 22 and 24 of the specimen 70.

In an investigation in which CrMoV and NiCrMoV alloys were used to form the HP and LP regions 22 and 24 of a rough-machined forging specimen (e.g., similar to the forging specimen 70 of FIG. 2), a series of five diametrical measurements, each series axially spaced about 20 to 100 millimeters from the adjacent series, were made consisting of two measurements at the outer surfaces of the forging specimen, at the axis of the specimen, and at radial midpoints between the outer surfaces and the axis. FIG. 4 is a graph plotting the nickel content (wt. %) versus axial location for each measured radial location of the specimen. To generate two-dimensional shapes from the data, an optimum curve was found that would fit the data points. While a continuous curve could be used, a linear three-step function is plotted in FIG. 4 by grouping the data points into three groups according to nickel content, one group being in the range of about 0.5% to about 2.25%, the second in the range of 2.25% to 3.2%, and the third in the range of 3.2% to 3.5%. Each group of data was fitted with a straight line using least square estimation on the condition that the two lines must share a common point at 2.25% and 3.2%.

Figure 5:
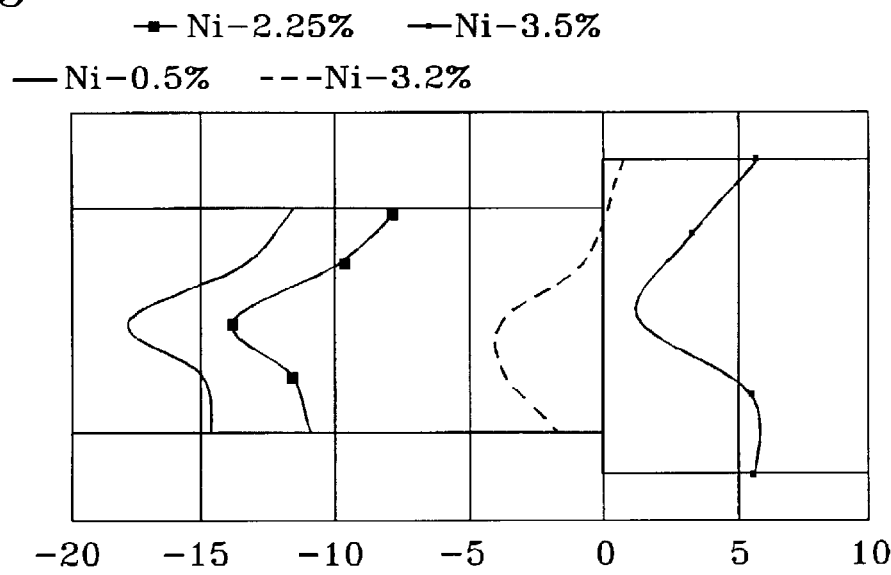
FIG. 5 is a two-dimensional plot generated from the data of FIG. 4 and identifying the boundaries of regions within the transition zone having different nickel contents.

After the function was determined, the axial location tion of 0.5%, 2.25%, 3.2%, and 3.5% nickel levels were calculated at the outer surface locations, the mid-radial locations, and the axis location. The axial location at the step transition was calculated because a step function to cover a range of 0.5% to 3.5% nickel content was used. The 0.5% and 3.5% nickel levels were chosen as generally corresponding to the levels of nickel for the CrMoV and NiCrMoV alloys, respectively, forming the regions of the specimen outside the transition zone, and therefore indicative of the boundaries of the transition zone. In the present example where each radial series consisted of five measurements, each boundary (nickel levels of 0.5% or 3.5%) of the transition zone and each subdivided zone was. located with at least five measured points. Several methods are available for fitting each of the five measurements to a two-dimensional curve. For example, different orders of polynomial or cubic spline curve fitting could be used. FIG. 5 illustrates the use of a cubic spline curve fitting, which is capable of generating a continuous, smooth curve that passes through each set of measurements corresponding to the same nickel level.

As evident from FIG. 5, each two-dimensional curve has an asymmetric shape relative to the axis of the specimen. As previously noted, this asymmetry is largely attributable to the forging operation, and would be detrimental to the thermal stability of a rotor machined from the specimen. The asymmetry of each two-dimensional is such that any attempt to establish three-dimensional axial boundaries (corresponding to nickel levels from 0.5% to 3.5%) by simply rotating the two halves of the curve on each side of the centerline at each nickel level would generate two volcano-shaped three-dimensional images of each boundary. To avoid this result, a suitable approach is to rotate each half of the curve through 180 degrees, gradually changing the shape of the curve during rotation so that the curve acquires the shape of the other half of the curve at the completion of the 180-degree rotation, so that the rotated curves coincide with each other when they meet. This can be achieved by assuming a two-dimensional curve function z=f(r), where r is the value for the radial direction and z is the value for the axial direction of a given point. Rotating a two-dimensional curve to generate a three-dimensional surface adds the variable θ, which is the variable for the circumferential direction. Using this technique, the equation to use is $$z(r, \theta) = z_1 \cos^2(\theta/2) + z_2 \sin^2(\theta/2) = f_1(r, \theta) \cos^2(\theta/2) + f(-r, \theta) \sin^2(\theta/2)$$

Figure 6:
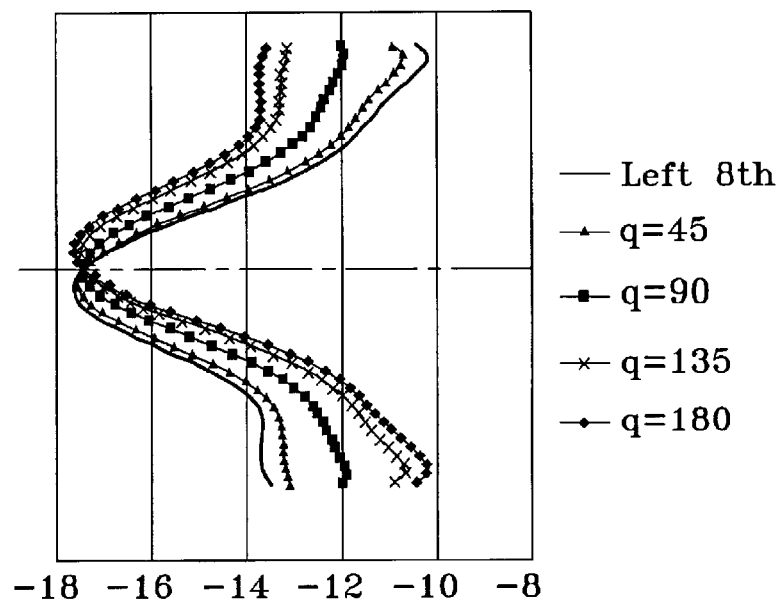
FIG. 6 represents a two-dimensional plot of one of the boundaries of FIG. 5 measured at a single cross-sectional and rotated to various circumferential positions to illustrate transformations used to model the asymmetry of the transition zone.
Figure 7:
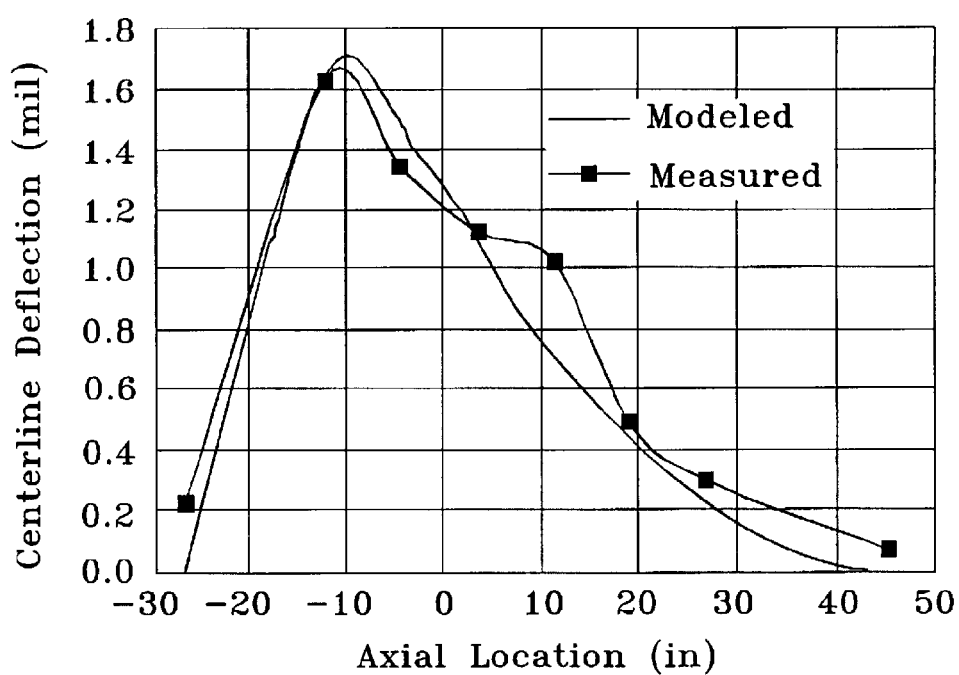
FIG. 7 is a graph comparing the predicted and measured centerline deflection along the axis of a rotor as a result of the asymmetry of the transition zone within the rotor, in which the predicted centerline deflection was based on a chemical analysis performed in accordance with the embodiment of FIGS. 2 and 4 through 6.

FIG. 6 shows the two-dimensional curve defining the 0.5% nickel boundary of FIG. 5 as its shape is modified when rotated through angles of 45, 90, 135 and 180 degrees in accordance with the above equation. From the three-dimensional contour defined by the curves of FIG. 6, a finite element model can be generated and used to predict the centerline deflection of a rotor machined from a similar rotor forging and then heated to some elevated temperature, e.g., a temperature to which the rotor would be subjected during its operation. More particularly, a three-dimensional approximation of the shape of the transition zone within a similarly-processed rotor forging having the same multiple alloy composition can be predicted by measuring the variation of chemistry at the outer surface of the rotor forging, and then utilizing the shape of the transition zone obtained from the analysis of the sectioned forging specimen. FIG. 7 shows the results of such analysis using a temperature of about 1150° F. (about 620° C.), and evidences that the predicted deflection profile is very close to the actual deflection profile of a rotor machined from a rotor forging produced by the same process as the forging specimen.

Figure 8:
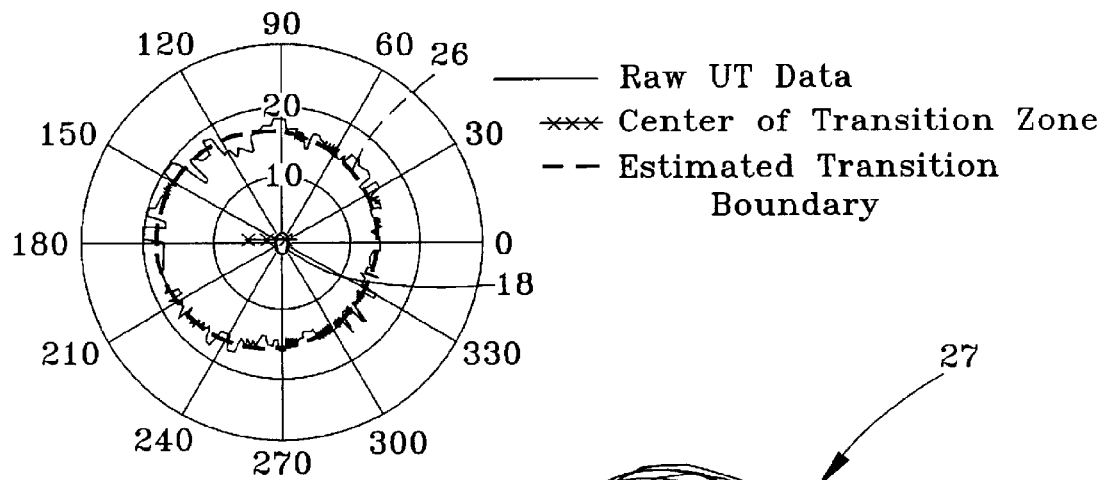
FIG. 8 is a chart showing data collected from an ultrasonic scan of the transition zone at one axial position of a rotor forging in accordance with the embodiment of FIG. 3.
Figure 9:
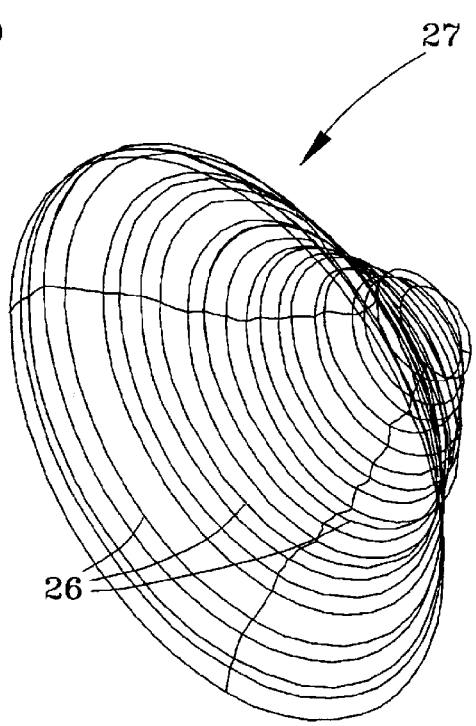
FIG. 9 is a three-dimensional plot generated using multiple ultrasonic scans similar to FIG. 8 and taken at multiple axial positions of a rotor forging.

FIG. 3 represents an alternative to the chemical analysis approach described above, in which the boundary points of the transition zone 20 are ascertained by ultrasonically examining the rough-machined forging 10. Such an approach is disclosed in copending and commonly-assigned U.S. patent application Ser. No. 10/463,441, incorporated herein by reference. In an investigation in which this approach was implemented in the present invention, an ultrasonic transducer 78 was placed against the outer surface of the forging 10, and ultrasonic energy was transmitted through the forging 10 along the transition zone 20 to detect changes in the response of the forging material to ultrasonic energy. As evidenced by FIG. 8, ultrasonic inspection of the forging 10 produced a noise pattern corresponding to variations in the metallurgical characteristics within the forging 10, such as differences in grain size attributable to the changes in chemistry between the transition zone 20 and the adjacent regions 22 and 24. After filtering the peak noise at each scan line, the data is fitted to a circular or elliptical contour 26 representative of the expected cross-sectional (two-dimensional) shape of each transition zone boundary. FIG. 9 represents a three-dimensional image 27 generated by combining multiple contours 26 taken along the length of the forging 10.

Figure 10:
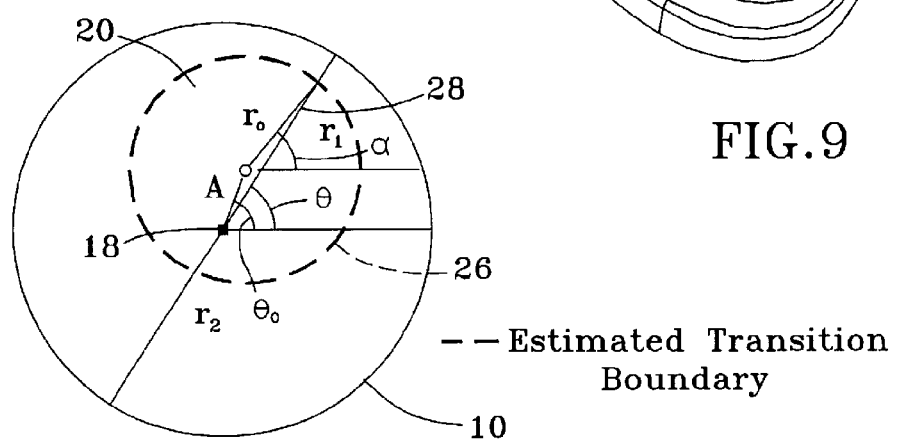
FIG. 10 represents an analytical technique for generating a three-dimensional mathematical model of the transition zone using the data of FIGS. 8 and 9.

Using the image of FIG. 9, a three-dimensional mathematical model was generated of the transition zone 20 by axially sectioning each transition zone contour 26 of the image with planes intersecting at the geometric centerline 18 of the forging 10. FIG. 10 represents one of the planes 28 intersecting one of the contours 26 at two points. Assuming the transition zone contour 26 has a radius $r_o$, the center of the contour 26 is offset from the forging centerline 18 a distance A at an angle $\theta_o$, and the plane 28 at an angle $\theta$ intersects the contour 26 to define radial distances $r_1$ and $r_2$ from the centerline 18, the following equations can be used to find the radial distances $r_1$ and $r_2$.

$$r_1 = A\cos(\theta_o-\theta)+(r_o^2-A^2\sin^2(\theta_o-\theta))^{1/2}$$

$$r_2 = -(-A\cos(\theta_o-\theta)+(r_o^2-A^2\sin^2(\theta_o-\theta))^{1/2})$$

If the total number of transition zone contours 26 is $N_c$, then a maximum of $2N_c$ number of intercept points are obtained by cutting the transition zone 20 with a plane 28 of at an angle $\theta$, and a maximum of $2N_cN_p$ intercept points can be obtained if the transition zone 20 is cut with $N_p$ number of planes 28. These intercept points can then be curve fit using polynomial or cubic spline curve fitting techniques. If a polynomial curve fitting technique is used, different orders are preferably tried until a good curve fit of the data (e.g., $R^2$ above 95%) is obtained. The peak position of each polynomial at different angles should also be consistent, i.e., all curves end up with the same peak. If a cubic spline fitting technique is used, an additional data point at the peak location is preferred. A set of curve fit coefficients from the previous step can then be used to interpolate points between intercepting points on adjacent scans within two adjacent angles, so that a three-dimensional model for the transition zone 20 can be mathematically constructed.

Figure 11:
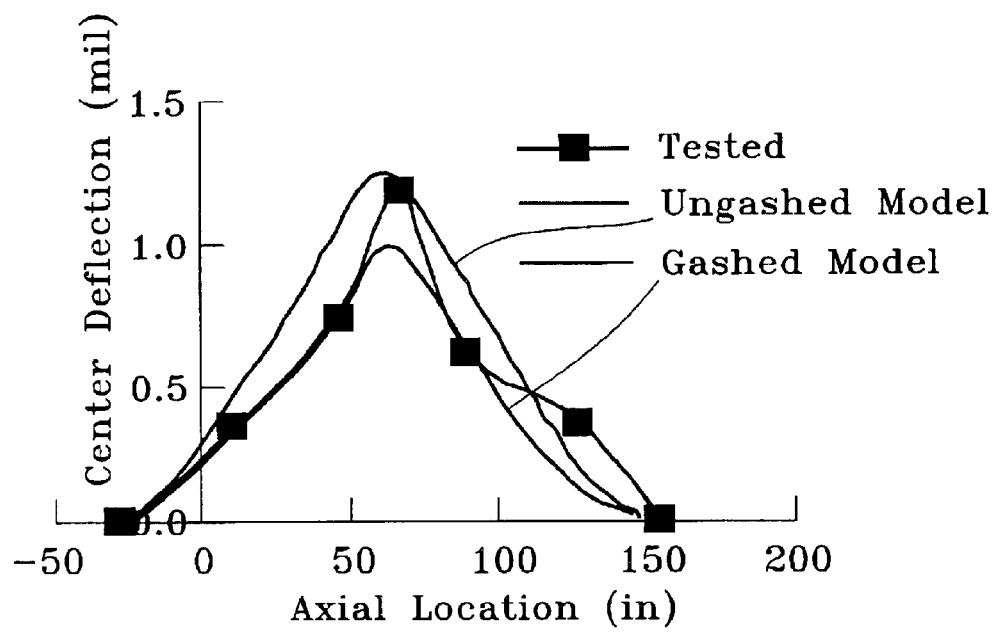
FIG. 11 is a graph comparing the predicted and measured centerline deflection along the axis of a rotor as a result of the asymmetry of the transition zone within the rotor, in which the predicted centerline deflection was based on an ultrasonic inspection performed in accordance with the embodiment of FIGS. 3 and 8 through 10.

In the investigation described above, the rotor forging 10 was produced from an ESR ingot in which the LP and IP/HP alloys were NiCrMoV and CrMoV, respectively. Assumptions for interpreting the ultrasonic data included a transition in the chemistry (and thus property) distribution occurred at a nickel content of about 3.0 weight percent, and that the ultrasonic inspection produced a noise pattern corresponding to variations in the metallurgical characteristics that occurred at the 3.0 wt. % nickel location. From the two-dimensional contours 26 and three-dimensional contour 27 defined in the manner described above, a three-dimensional finite element model was generated and used to predict the centerline deflection of a rotor machined from the rotor forging 10 and then heated to some elevated temperature, e.g., a temperature to which the rotor would be subjected during its operation. FIG. 11 shows the results of such analysis using a furnace with three different temperature zones (about 400, 800 and 1000° F. (about 200, 425, and 540° C.)) to simulate the variation of temperature along the length of a rotor during operation, and evidences that the predicted deflection profile was very close to the actual deflection profile of the machined rotor. This model was also able to predict the rotor centerline deflection before and after removing (gashing) the material between wheels of the rotor.

Finally, to reduce the amount of centerline deflection from that predicted through the above-described modeling techniques, a new rotor axis is identified that is more centrally located within the transition zone 20 than the forging centerline 18, while still within machining tolerances. The forging (or, more typically, a rough-machined geometry formed by rough machining the forging) can then be off-center machined to establish the new axis as the geometric centerline (and therefore the axis of rotation) of the final machined rotor geometry. The methodology involves translating the coordinates of the rough-machined forging from the geometric centerline of the forging to the new axis, which is at or near the center of a three-dimensional approximation of the transition zone 20.

Figure 12:
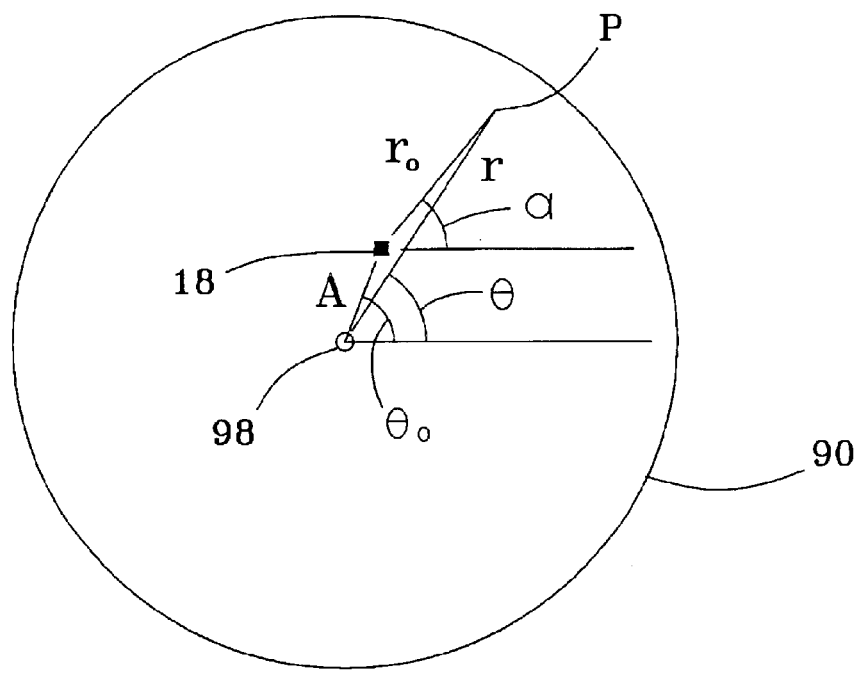
FIG. 12 represents an analytical technique for transforming the coordinate system of a rotor to a new coordinate system whose center is more centrally located within the transition zone to reduce rotor centerline deflection.

To explain the methodology, reference is made to FIG. 12 which shows the machined outer profile of a rotor 90 at one axial position. For illustrative purposes, the rotor 90 is indicated as having an as-forged geometric centerline 18, corresponding to the rough-machined forging 10 of FIG. 3. The location for the new rotor axis, more centrally located within the rotor 90 (and approximately centrally located within the transition zone 20 of the forging 10), is identified with reference number 98. The offset of the new rotor axis 98 relative to the forging centerline 18 is exaggerated to assist in clarifying the methodology. In FIG. 12, the new rotor axis 98 is offset a distance A and on an angle $\theta_o$ from the forging center-line 18. A point P is located a distance $r_o$ and at an angle $\alpha$ relative to the forging centerline 18, and a distance r and at an angle $\theta$ relative to the new rotor axis 98. The coordinates (r,$\theta$) in the coordinate system with its center at the axis 98 can be obtained with the following equations:

$$r_o = [(r^2+A^2-2Ar\cos(\theta-\theta_o)]^{1/2}$$

$$\tan\alpha = (r\sin\theta - A\sin\theta_o)/(r\cos\theta - A\cos\theta_o)$$

As atan(x) is in the range of −90 to +90 degrees, and the angle in a cylindrical coordinate system is in the range of −180 to +180 degrees, the following table can be used to obtain angle $\alpha$.

| $\alpha=$ | $(r\cos\theta-\alpha\cos\theta_0) > 0$ | $(r\cos\theta-\alpha\cos\theta_0) < 0$ |
|---|---|---|
| $(r\sin\theta-\alpha\sin\theta_0) > 0$ | $\operatorname{atan}\dfrac{r\sin\theta - a\sin\theta_0}{r\cos\theta - a\cos\theta_0}$ | $\operatorname{atan}\dfrac{r\sin\theta - a\sin\theta_0}{r\cos\theta - a\cos\theta_0} + 180°$ |

-continued

| $\alpha=$ | $(r\cos\theta - \alpha\cos\theta_0) > 0$ | $(r\cos\theta - \alpha\cos\theta_0) < 0$ |
|---|---|---|
| $(r\sin\theta - \alpha\sin\theta_0) < 0$ | $\operatorname{atan}\dfrac{r\sin\theta - a\sin\theta_0}{r\cos\theta - a\cos\theta_0}$ | $\operatorname{atan}\dfrac{r\sin\theta - a\sin\theta_0}{r\cos\theta - a\cos\theta_0} - 180°$ |

This table can be summarized by one common equation as:

$$\alpha = A\tan\frac{r\sin\theta - A\sin\theta_0}{r\cos\theta - A\cos\theta_0} + 90° \times \left(1 - \frac{r\cos\theta - A\cos\theta_0}{|r\cos\theta - A\cos\theta_0|}\right) \times \frac{r\sin\theta - A\sin\theta_0}{|r\sin\theta - A\sin\theta_0|}$$

By translating the rotor geometry to the new coordinate system with the off-center magnitude A and the offset set angle α from the forging centerline 18, all points based on a three-dimensional model generated as described above are translated to the new coordinate system with its center at centerline 98. In this manner, any axial position in the transition zone of the forging 10 can be machined using the new coordinate system so the axis of rotation of the machined rotor 90 coincides with the axis 98, and therefore is more centrally located with respect to the three-dimensional approximation of the shape of the transition zone 20 of the rough-machined forging 10. In so doing, the axis of rotation of the machined rotor 90 is also more centrally located with respect to the material properties of the forging 10 than was the geometric centerline 18 of the forging 10. As a result, the machined rotation 90 is able to exhibit less deflection when heated and rotated about its axis of rotation 98 than would the machined rotor if it had been machined so that its axis of rotation coincided with the geometric centerline 18 of the forging 10.

The procedure just described can be repeated at several positions along the length of the transition zone. The results of the several calculations can be analyzed using finite element techniques in conjunction with optimization techniques to select the best choice of off-center machining. Based on the new rotor axis 98 identified by the above process, thermal analysis can be performed to obtain the temperature gradient of the entire rotor 90 to permit recalculating of the predicted rotor centerline deflection. To find the optimum location of the new rotor axis 98, the largest possible off-center machine tolerances can be calculated based on the difference between the diameter of the rotor 90 at its rough-machined geometry and the diameter of the rotor 90 at its final machined geometry. Using the off-center machine distance A and the off-center angle α as variables, and the maximum rotor centerline deflection as response, a series of runs and analysis-evaluation-modification cycles can be performed with random variable inputs for A and α. A response curve can then be generated using least square curve fitting between data points to identify the minimum centerline deflection within the allowed range for off-center shift. In one investigation implementing the above-described methodology, relocating the rotor axis 98 a distance of about 12 mm from the original rough-machined centerline 18 reduced centerline deflection by about 65%.

While the invention has been described in terms of one or more particular embodiments, it is, apparent that other forms could be adopted by one skilled in the art. Therefore, the scope of the invention is to be limited only by the following claims.

What is claimed is:

1. A monolithic rotor formed by machining a rotor forging, the monolithic rotor comprising first and second rotor regions axially aligned within the monolithic rotor and a transition zone therebetween, the first and second rotor regions being formed of different alloys and the transition zone having a composition that differs from and varies between the first and second rotor regions, the transition zone having a three-dimensional shape about a centerline of the rotor forging, the monolithic rotor having an axis of rotation that is more centrally located with respect to the transition zone than the centerline of the rotor forging.

2. The monolithic rotor according to claim 1, wherein the axis of rotation of the monolithic rotor is more centrally located with respect to material properties of the monolithic rotor than the centerline of the rotor forging.

3. The monolithic rotor according to claim 1, wherein the first rotor region is located within a high pressure region of the monolithic rotor and is formed from an alloy chosen from the group consisting of CrMoV low alloy steels, martensitic stainless steels containing about 11 to about 14 weight percent chromium, Fe-Ni alloys, and nickel-base alloys, and the second rotor region is located within a low pressure region of the monolithic rotor and is formed from an alloy chosen from the group consisting of NiCrMoV low alloy steels and martensitic stainless steels containing about 11 to about 14 weight percent chromium.

4. The monolithic rotor according to claim 1, wherein the rotor is a stream turbine rotor.

5. A steam turbine in which the monolithic rotor according to claim 1 is installed.

6. The monolithic rotor according to claim 1, wherein the rotor is a gas turbine engine rotor.

7. A gas turbine engine in which the monolithic rotor according to claim 6 is installed.

8. The monolithic rotor according to claim 1, wherein the rotor is a jet engine rotor.

9. A jet engine in which the monolithic rotor according to claim 8 is installed.

\* \* \* \* \*

UNITED STATES PATENT AND TRADEMARK OFFICE
CERTIFICATE OF CORRECTION

| | |
|---|---|
| PATENT NO. | : 6,971,850 B2 |
| APPLICATION NO. | : 10/701306 |
| DATED | : December 6, 2005 |
| INVENTOR(S) | : Swami Ganesh et al. |

It is certified that error appears in the above-identified patent and that said Letters Patent is hereby corrected as shown below:

On the title page item (75),
Two inventors were mistakenly omitted from the printed patent certificate. Add these two inventors to the bottom of the list of inventors:

Francis Alexander Reed
Robert V. Falsetti

Signed and Sealed this

Seventeenth Day of October, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,971,850 B2 | Page 1 of 1 |
| APPLICATION NO. | : 10/707306 | |
| DATED | : December 6, 2005 | |
| INVENTOR(S) | : Swami Ganesh et al. | |

It is certified that error appears in the above-identified patent and that said Letters Patent is hereby corrected as shown below:

On the title page item (75),
Two inventors were mistakenly omitted from the printed patent certificate. Add these two inventors to the bottom of the list of inventors:

Francis Alexander Reed
Robert V. Falsetti

This certificate supersedes Certificate of Correction issued October 17, 2006.

Signed and Sealed this

Twenty-eighth Day of November, 2006

JON W. DUDAS
*Director of the United States Patent and Trademark Office*